United States Patent [19]
Verhoff et al.

[11] Patent Number: 6,114,577
[45] Date of Patent: Sep. 5, 2000

[54] DESORPTION PROCESS AND APPARATUS

[75] Inventors: Francis H. Verhoff, Cincinnati, Ohio; Martin Grendze, Indianapolis, Ind.

[73] Assignee: Reilly Industries, Inc., Indianapolis, Ind.

[21] Appl. No.: 08/693,216

[22] PCT Filed: Feb. 15, 1995

[86] PCT No.: PCT/US95/01980

§ 371 Date: Oct. 23, 1996

§ 102(e) Date: Oct. 23, 1996

[87] PCT Pub. No.: WO95/21810

PCT Pub. Date: Aug. 17, 1995

[51] Int. Cl.$^7$ ............................................... C07C 51/42
[52] U.S. Cl. ..................... 562/580; 562/584; 562/589; 210/177; 210/269; 210/284
[58] Field of Search .................... 562/580, 584, 562/589; 210/177, 269, 284

[56] References Cited

U.S. PATENT DOCUMENTS

| | | |
|---|---|---|
| 4,323,702 | 4/1982 | Kawabata et al. . |
| 4,522,726 | 6/1985 | Berry et al. . |
| 4,720,579 | 1/1988 | Kulprathipanja . |
| 4,764,276 | 8/1988 | Berry et al. . |
| 4,808,317 | 2/1989 | Berry et al. . |
| 4,851,573 | 7/1989 | Kulprathipanja et al. . |
| 4,851,574 | 7/1989 | Kulprathipanja et al. . |

FOREIGN PATENT DOCUMENTS

| | | |
|---|---|---|
| 0 377 430 A1 | 7/1990 | European Pat. Off. . |
| 855155 | 9/1985 | South Africa . |
| WO 92/16490 | 10/1992 | WIPO . |
| WO 92/16534 | 10/1992 | WIPO . |
| WO 93/06226 | 4/1993 | WIPO . |

*Primary Examiner*—Paul J. Killos
*Attorney, Agent, or Firm*—Woodard, Emhardt, Naughton, Moriarty & McNett

[57] ABSTRACT

Described are preferred processes and apparatuses for thermally desorbing desired chemical products from resins to which they are adsorbed. The processes and apparatuses provide highly efficient use of applied heat throughout resin preheat, desorption and cooling phases.

49 Claims, 3 Drawing Sheets

DESORPTION PROCESS AND APPARATUS

BACKGROUND OF THE INVENTION

The present invention relates generally to solid-phase adsorption/desorption techniques for recovering valuable chemical products. More particularly, the invention relates to highly efficient and economic processes for thermally desorbing adsorbed products, and apparatuses useful in conducting the processes.

As further background, the recovery and purification of carboxylic acids and other valuable chemical products from mediums has long been studied in an effort to discover efficient, cost-effective routes for their production. For example, carboxylic acids such as citric acid and lactic acid are manufactured by fermentation in large scale worldwide. Such fermentations provide fermentation broths from which the desired acid must be recovered and purified. Where high volume manufacture is involved, the importance of keeping recovery costs to a minimum cannot be overemphasized.

Recent recovery work has focused on the use of solid polymeric adsorbent materials to recover carboxylic acids from fermentation mediums. In this approach, the fermentation broth is passed over the adsorbent which adsorbs the carboxylic acid, and the carboxylic acid is desorbed in some fashion to provide product. Generally, a wide variety of adsorbents and adsorption/desorption schemes have been proposed.

For example, Kawabata et al., U.S. Pat. No. 4,323,702, describe a process for recovering carboxylic acids with a material of which the main component is a polymeric adsorbent having a pyridine skeletal structure and a cross-linked structure. The carboxylic acid is adsorbed on the adsorbent, and then desorbed using a polar organic material such as an aliphatic alcohol, ketone or ester. However, these polar organics can be difficult to separate from the eluted medium, and/or can cause significant side reaction(s) during operations such as distillation necessary for the separation.

Kulprathipanja et al., in U.S. Pat. Nos. 4,720,579, 4,851,573, 4,851,574, teach solid polymeric adsorbents including a neutral, nonionic, macroreticular, water-insoluble cross-linked styrene-poly(vinyl)benzene, a cross-linked acrylic or styrene resin matrix having attached tertiary amine functional groups or pyridine functional groups, or a cross-linked acrylic or styrene resin matrix having attached aliphatic quaternary amine functional groups.

In their work, Kulprathipanja et al. describe "pulse tests" in which they identify acetone/water, sulfuric acid, and water as desorbents. Needless to say, an acetone/water desorbent leads to organic materials in the desorbed fraction and attendant disadvantages as discussed above. When sulfuric acid is used as desorbent, it of course is present in the eluted fraction and complicates product recovery. Moreover, although they name water as a potential desorbent, Kulprathipanja et al. indicate its unfeasibility in their processes, directing in their '573 patent that water "is not strong enough to recover the absorbed citric acid quickly enough to make the process commercially attractive."

South African Patent Application No. 855155, filed Jul. 9, 1985, describes processes in which product acids were recovered from their aqueous solutions. In the adsorption step, the acid-containing solution was passed through a column containing an adsorber resin consisting of a vinylimidazole/methylene-bis-acrylamide polymer, a vinylpyridine/trimethylolpropane tri-methacrylate/vinyltrimethylsilane polymer, a vinylimidazole/N-vinyl-N-methylacetamide/methylene-bis-acrylamide polymer, Amberlite IRA 35 (Rohm & Haas—acrylate/divinylbenzene based polymer containing dimethylamino groups), or Amberlite IRA 93 SP (Rohm & Haas) or Dowex MWA-1 or WGR-2 (Dow Chemical) (these latter three being styrene/divinylbenzene based polymers containing dimethylamino groups). To desorb the acid, water, usually at a temperature of 90° C., was allowed to pass through the column. However, the single-pass elution process described involves an inefficient use of heat energy and does not substantially maximize the potential use of the resins to achieve highly concentrated desorbed solutions. Additionally, resins employed in this South African application are relatively thermally instable and thus substantially degrade during desorption procedures employing hot water.

International Applications PCT/US92/02107 filed Mar. 12, 1992 (published Oct. 1, 1992, WO 92/16534) and PCT/US92/01986 filed Mar. 12, 1992 (published Oct. 1, 1992, WO 92/16490) both by Reilly Industries, Inc., disclose desorbing lactic and citric acid, respectively, from divinylbenzene crosslinked vinylpyridine or other resins using steam or hot water. The resins employed have advantageous adsorption/desorption capacities and are highly thermally stable under the described hot water desorption procedures. Nonetheless, improved processes would provide greater efficiency in the use of heat applied to the desorption and would readily provide desorbed solutions of even higher product concentration.

In light of this and other background in the area, there remains a need for improved, effective processes for recovering carboxylic acids and other valuable products from their dilute solutions. The present invention addresses these needs.

SUMMARY OF THE INVENTION

Accordingly, preferred embodiments of the invention provide desorption processes in which thermal energy is efficiently utilized in the thermal desorption of resin-adsorbed products, and/or in which resin rinse or wash operations are conducted with product mediums to reduce product losses while nonetheless providing an effective rinse. Thus, in accordance with one aspect of the invention, a thermal desorption process includes establishing a process wherein an amount of adsorbent is substantially fully loaded with an adsorbed product, the loaded adsorbent is rinsed with a rinse agent, and the loaded adsorbent is then treated with a heated desorbing agent to form a product-containing medium. In the inventive processes the rinse agent in these steps contains an amount of the product to promote retention of (i.e. decrease removal of) the adsorbed product on the adsorbent, and the product-containing medium is passed through a heated heat exchanger and into the same or another amount of product-loaded adsorbent, to further enrich the product-containing medium in the product.

Another preferred aspect of the invention provides a thermal desorption process which includes establishing a process wherein an amount of adsorbent is substantially fully loaded with an adsorbed product, the loaded adsorbent is rinsed with a rinse agent, and the loaded adsorbent is then treated with a heated desorbing agent to form a product-containing medium. In accordance with the invention the product-containing medium is passed through a heated heat exchanger and into the same or another amount of product-loaded adsorbent, to enrich the product-containing medium in the product. For instance, focusing on the desorption step, processes in accordance with this embodiment can include a first desorption step conducted by passing a heated liquid desorbent through a contacting zone containing a solid adsorbent resin, so as to desorb adsorbate or product from the resin. After the first desorption step, the product-containing desorbent is passed through a heat exchange zone in which additional heat is transferred to the liquid desorbent. The heated desorbent is then subjected to a second desorption step in which it is passed through a contacting zone (the same or another contacting zone) containing solid adsorbent resin to desorb product from the resin and further enrich the product-containing desorbent in product.

Particularly preferred inventive processes employ a plurality of resin-filled contacting zones (e.g. resin columns) loaded with product. The heated desorbent medium is passed through a first loaded column to desorb product and then through a heat exchange zone where additional heat is transferred to the medium. The heated desorbent medium is then passed through a second loaded column to desorb product and become more enriched in product. Prior to reaching the desorbent steps, the resin-filled contacting zones are preferably preheated by contact with heated, product-containing desorbent medium which is the product from one or more previous desorption steps. This resin-preheating step also serves to cool the product-rich desorbent medium, thus making efficient use of thermal energy in the system. Moreover, after the desorption step(s), the resin-filled contacting zone (now substantially stripped of product) is preferably subjected to a cooling step so as to obtain optimum temperatures for the adsorption zone in the next cycle. The preferred cooling step includes passing a liquid medium at a temperature lower than the resin through the contacting zone, and then passing the medium through a heat exchange zone to remove heat from the medium. One preferred cooling step also includes using cold product-depleted feed solution (waste) as the heat-transfer medium so as to make efficient use of the thermal energy in the system. Processes of the invention can be carried out in apparatuses appropriately valved to sequentially subject the contacting zones to preheat, desorption, and cooling steps.

Accordingly, a further preferred embodiment of the invention provides a thermal desorption process which comprises the following steps:

(a) providing a plurality of chambers having inlet ports and outlet ports and containing a solid adsorbent resin loaded with product;

(b) advancing the chambers sequentially past a plurality of supply ports to cooperate with the inlet ports and discharge ports to cooperate with the outlet ports;

(c) introducing a heated desorbent liquid into a first of the chambers through a first of the supply ports, the desorbent liquid passing over the adsorbent resin in the first chamber and exiting through a first of the discharge ports as a first product-containing medium;

(d) passing the first product-containing medium after step (c) through a heat exchange zone wherein it is heated;

(e) conducting the heated medium after step (d) through a second of the supply ports and into a second of the chambers, the product-containing medium passing over the loaded adsorbent resin in the second chamber and exiting through a second of the discharge ports as a second product-containing medium enriched in product as compared to the first product-containing medium.

In accordance with another aspect of the invention, a desorption process includes establishing a process wherein a plurality of contacting zones containing adsorbent are sequentially processed, the processing including substantially fully loading the adsorbent with an adsorbed product, rinsing the adsorbent with a rinse agent, and then treating the adsorbent with a desorbing agent to form a product-containing medium. In this aspect of the invention, a portion of the product-containing medium from a prior-processed contacting zone is included in the rinse agent in the processing of a subsequent contacting zone to decrease removal of the adsorbed product from the adsorbent during the rinsing step.

Again, particularly preferred processes employ a plurality of resin-filled contacting zones (e.g. resin columns) loaded with product, which are subjected to rinse and then desorption steps. Desorbent medium, preferably heated, is passed through a first loaded column to desorb product and form a product-containing medium. A first portion of the product-containing medium can be isolated as product, and a second portion of the product-containing medium is then passed through a second product-loaded column in a rinse operation to remove undesired, non-adsorbed or lesser-desorbed materials from the resin. Prior to reaching the rinse operation, the second portion of the product-containing medium is preferably cooled or allowed to cool, for example employing a cooled heat exchanger. As before, processes of this aspect of the invention can also be carried out in apparatuses appropriately valved to sequentially subject the contacting zones to preheat, desorption, and cooling steps.

Accordingly, particularly preferred modes of carrying out this aspect of the invention comprise the following steps:

(a) providing a plurality of chambers having inlet ports and outlet ports and containing a solid adsorbent resin loaded with adsorbed product;

(b) advancing the chambers sequentially past a plurality of supply ports to cooperate with the inlet ports and discharge ports to cooperate with the outlet ports;

(c) introducing a desorbent liquid into a first of the chambers through a first of the supply ports, the desorbent liquid passing over the adsorbent resin in the first chamber and exiting through a first of the discharge ports as a product-containing medium;

(d) conducting a portion of the product-containing medium after step (c) through a second of the supply ports which precedes the first supply port, and into a second of the chambers, the desorbent liquid passing over and rinsing the adsorbent resin in the second chamber and exiting through a second of the discharge ports.

Other preferred embodiments of the invention provide a desorption apparatuses. One apparatus of the invention comprises a plurality of resin columns containing adsorbent resin, and liquid-circulating means for passing desorbent liquid sequentially through the resin columns. The liquid-circulating means includes at least a first heat exchanger adapted to heat liquid after exiting one of the resin columns and prior to entering another of the columns. The liquid-circulating means also preferably includes a second heat exchanger downstream of the first heat exchanger (i.e. which becomes associated with the resin columns subsequent to the first heat exchanger) and which is adapted to cool liquid after exiting one of the columns and prior to entering another. Additional features and preferred apparatuses of the invention are discussed below, and include further heat exchangers to preheat the resin columns as well as advantageous carousel devices incorporating heat exchangers to achieve resin column preheating, desorption and cooling functions.

The inventive processes and apparatuses provide for the recovery of products in concentrated liquid mediums while efficiently utilizing thermal energy to aid in the recovery, and also while operating in configurations which reduce product loss from wash operations and thus provide more product-concentrated desorbed mediums. The invention also provides processes and apparatuses which are easy to operate, and which can be employed to recover a wide variety of desired product products in concentrated solutions. Additional preferred embodiments, features and advantages of the invention will be apparent from the following description.

DESCRIPTION OF THE PREFERRED EMBODIMENT

Figure 1:
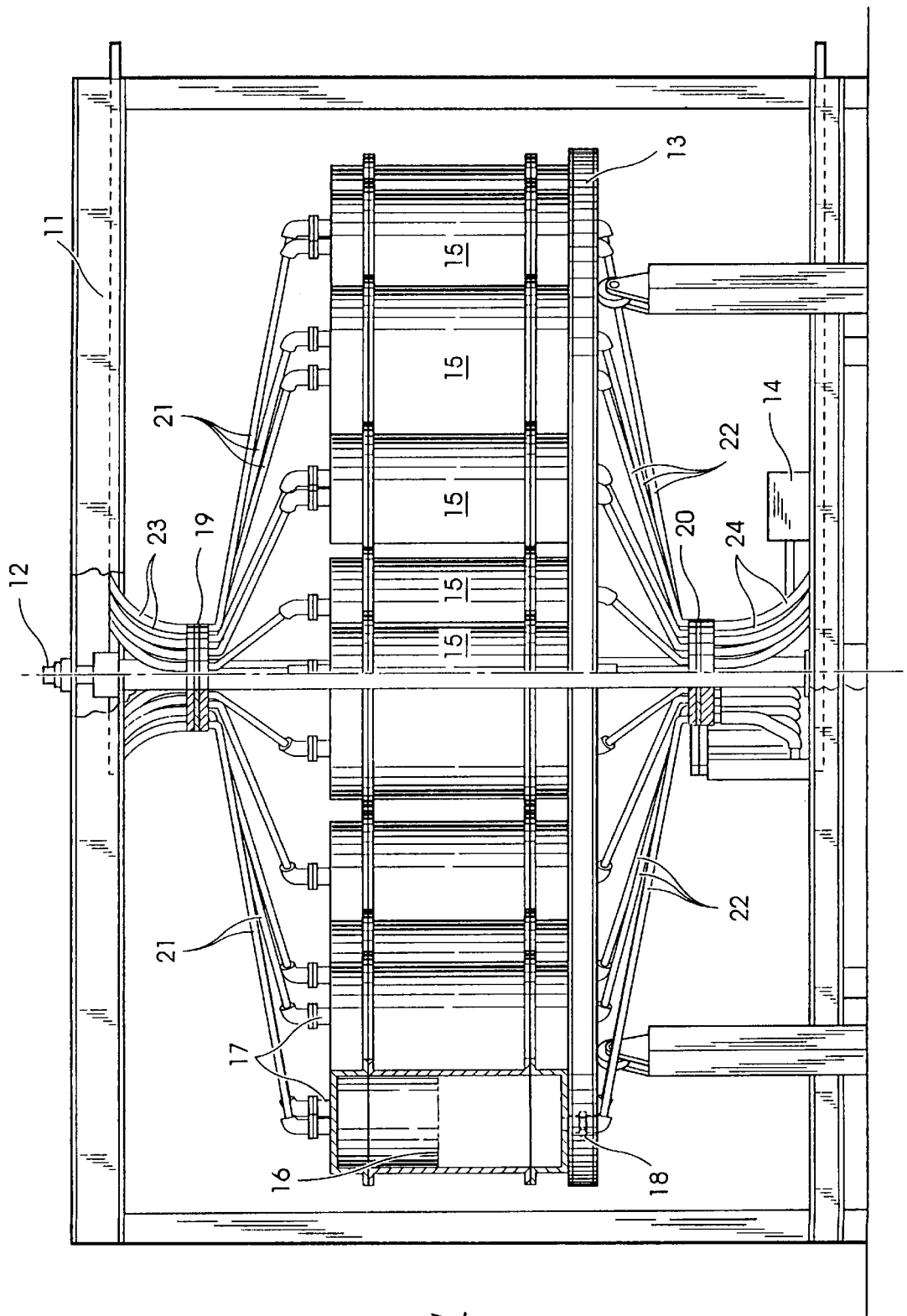
FIG. 1 is a side elevational view partially in cross-section of an illustrative continuous contacting apparatus which can be used in the present invention.

For the purposes of promoting an understanding of the principles of the invention, reference will now be made to certain of its embodiments and specific language will be used to describe the same. It will nevertheless be understood that no limitation of the scope of the invention is thereby intended, such alterations and modifications and applications of the principles of the invention as described herein being contemplated as would normally occur to one skilled in the art to which the invention pertains.

As indicated above, a preferred process of the invention provides thermal desorption of an product from an adsorbent resin. As discussed previously, in general, adsorption/desorption processes for recovering valuable chemical products are known, and a wide variety of adsorbent resins and appropriate liquid desorbents have been identified. Thus, those ordinarily skilled in the art will be readily able to select and use suitable adsorbent resins and desorbent mediums in accordance with the present invention.

Generally speaking, the adsorbent employed will have the capacity adsorb the desired product, and will be stable (i.e. will not undergo substantial degradation) under the processing conditions utilized as further described below. Although the adsorbent can be any substance capable of adsorbing the desired product (including activated carbon, zeolites, etc.), more desirable adsorbents for use in the invention will be polymeric adsorbent resins which are crosslinked to provide thermal and mechanical stability and an advantageous physical form. Bead-form adsorbent resins are preferred, especially those having a particle size of about 20 to about 100 mesh, more especially about 40 to about 60 mesh.

A wide variety of suitable polymeric adsorbents have been reported for the recovery of desired adsorbate products such as carboxylic acids. These polymeric adsorbent are formed through the polymerization of one or more monomers usually including a crosslinking monomer. The polymerization is carried out to provide resin beads in either gel or macroreticular form. Further, these resin beads can be chemically modified, e.g. by adding ionic groups to the resin such as quaternary salt or acid salt groups. The resulting resin can thus be anionic, cationic or nonionic and have a variety of physical and chemical characteristics. This variety of polymers is known in the art for use as adsorbents. For example, suitable reported resins include nonionic and ionic polymers, including neutral, noniogenic, macroreticular, water-insoluble cross-linked styrene-poly(vinyl)benzene, basic polymer materials such as crosslinked pyridine-containing polymers, e.g. vinylpyridine polymers, cross-linked acrylic or styrene resin matrices having attached tertiary amine functional groups or pyridine functional groups, cross-linked acrylic or styrene resin matrices having attached aliphatic quaternary amine functional groups, and the like (see e.g. Kawabata and Kulprathipanja et al. patents cited in the Background). These and numerous other polymers known in the art for use as adsorbents, for example base or acid ion exchange resins including styrenic, acrylic, epoxy amine, styrene polyamine, and phenol formaldehyde, or nonionic adsorption resins, will be suitable for use in temperature swing adsorption/desorption processes in accordance with the invention; preferably, however, the polymer adsorbent will be a crosslinked base polymer, such as a crosslinked polymer containing N-aliphatic or N-heterocyclic tertiary amine functions, for example polymers containing dialkylamino or pyridine functionalities.

Particularly preferred pyridine-containing polymers are polyvinylpyridine polymers such as poly 2- and poly 4-vinylpyridine gel or macroreticular resins exhibiting a bead form. These resins are preferably at least about 2% cross-linked with a suitable cross-linking agent, desirably a divinyl crosslinking agent (i.e. a crosslinking agent having two vinyl moieties) such as divinylbenzene. More preferred resins are 2 to 25% crosslinked bead-form vinylpyridine polymers, e.g. poly 2- and poly 4-vinylpyridine polymers.

For example, more preferred resins include poly 2- and poly 4-vinylpyridine resins available from Reilly Industries, Inc., Indianapolis, Ind., in the REILLEX™ polymer series. These REILLEX™ polymers are 2% or 25% crosslinked, and exhibit good thermal stability and adsorptive and desorptive capacities and other preferred features as described herein. For example, preferred resins of this type have exhibited desorptive capacities of at least about 200 mg citric acid per gram of polymer. Additional preferred resins are available from this same source under the REILLEX™ HP polymer series. These REILLEX™ HP polymers also exhibit advantageous capacities, and are highly regenerable. For more information about these REILLEX™ polymers, reference can be made to the literature, including that available from Reilly Industries, Inc. in the form of REILLEX™ reports 1, 2 and 3.

AMBERLYST A-21 resin from Rohm and Haas, Philadelphia, Pa. can also be used in the invention. This A-21 resin is crosslinked by divinylbenzene (greater than 2%) and contains aliphatic tertiary amine functions (particularly, attached dialkylamino (dimethylamino) groups). For additional information about this and other similar resins, reference can be made to the literature including that available from the manufacturer. See, e.g., AMBERLYST A-21 technical bulletin fluid process chemicals," Rohm and Haas, April 1977.

In accordance with the invention, the method by which the product is adsorbed onto the resin can be conventional. In some fashion or another, methods for loading the adsorbent with product involve contacting the resin with a liquid (usually but not necessarily aqueous) medium containing product under appropriate conditions for adsorption. This contacting may be performed in any suitable apparatus, for example in columns containing the adsorbent resin through the medium is passed, as further discussed below. It is preferred to substantially load the adsorbent resin with product, that is, to continue loading the resin with product until the resin's adsorptive capacity is substantially exhausted. For example, in preferred inventive processes, the adsorbent resin will be at least 50% loaded with product (i.e. 50% of the resin's total capacity to adsorb the product is depleted), more preferably at least 80% loaded with product. In general, higher levels of loading will result in a more effective uses of the resin; however, it will be understood that the most efficient and economic loading levels may vary from process to process and determining and achieving such levels will fall within the purview of the skilled worker given the teachings herein.

Thermal desorption processes of the invention will generally find utility if the heat of reaction between the product and the adsorbent is significant, e.g. such that the adsorbent has a substantially greater capacity to adsorb the adsorbent at relatively low temperatures as compared to higher temperatures. Of particular interest in the invention is the recovery of organic acids, especially carboxylic acids such as aliphatic carboxylic acids, from mediums in which they have been produced by fermentation, i.e. by the fermentation of suitable carbon sources by microorganisms. The commercial success of such fermentation processes depends heavily upon the ability to effectively recover product acids from their formed, relatively dilute solutions.

For example, substantial worldwide production of organic carboxylic acids such as citric and lactic acids is performed by fermentation. In the case of citric acid, the broth may be from a fermentation of a carbon source such as corn sugar or molasses with a suitable citric-acid-producing bacteria or other microorganism such as *Aspergillus niger*. Lactic acid is produced using bacteria or other microorganisms capable of forming lactic acid upon metabolizing a carbon source. Typically, bacteria of the Family Lactobacillaceae are employed, although other microorganisms such as fungi may be used. For example, fungi of the family Rhizopus, such as *Rhizopus oryzae* NRRL 395 (United States Department of Agriculture, Peoria, Ill.), can be employed to produce substantially pure L+ lactic acid as generally taught in International Application No. PCT/US92107738 filed Sep. 14, 1992 by Reilly Industries, Inc. (published Apr. 1, 1993, WO 93/06226). It is well within the purview of the skilled artisan to select and use suitable fermentation organisms to produce fermentation broths containing organic acids such as carboxylic acids, which broths can be treated in accordance with the invention to recover the acids.

When a carboxylic acid-containing fermentation medium is involved, it will usually contain water, the product acid, salts, amino acids, sugars, and other various components in minor amounts. Such fermentation mediums can be filtered to remove suspended solids prior to the adsorption step. Similarly, after loading the adsorbent with the product, it will often be desirable to rinse the loaded polymer with cold water or another suitable agent to wash away any salts or other materials desirably kept out of the desorbed product-enriched medium. Of course, the rinse temperature, agent and other factors will be designed to maximize removal of undesired residues, and minimize removal of the product of interest, from the resin bed. These and similar details in the general practice of the invention will readily occur to those practiced in the relevant field.

A feature of the invention, however, relates to the discovery of process configurations which can be used to increase the concentration of the desired product in the product streams and minimize product loss to waste. Generally in these configurations, after the adsorbent resin has been loaded with product, the loaded resin bed is rinsed using a rinse medium containing the product. It has been discovered that such product streams, for example resultant of a prior desorption operation to recover the product, can be used to effectively rinse undesired, non-adsorbed or relatively weakly-adsorbed residues such as sugars from the resin bed. At the same time, the presence of product in the rinse agent has been found to increase retention of adsorbed product on the resin during the rinsing operation, thus leading to increased efficiencies in the use of the resin capacity for the product and increased concentrations of the product in the final product stream. Thus, in preferred operations a portion of the product stream from the overall adsorption-rinse-desorption process can be diverted to the rinse step in order to provide an increase in concentration of the product in the desorbed stream.

A variety of liquid desorbents or desorbing agents can be employed in the present invention. These desorbents include, for example, organic solvents, e.g. polar organic solvents such as alcohols, ketones and esters, as well as aqueous mediums such as water (i.e. substantially pure water without added solutes), aqueous solutions of acids or bases, e.g. hydrochloric acid, sulfuric acid or sodium hydroxide solutions, or water/organic co-solvent mediums such as water/alcohol mixtures. More preferred inventive processes employ water so as to provide desorbate mediums free from unnecessary solutes or co-solvents which may complicate recovery of the desired product.

Generally, thermal desorptions of the invention will occur at elevated temperatures sufficient to desorb the product from the adsorbent resin, and at which the resin and product are thermally stable. In preferred processes utilizing aqueous desorbents such as water, the desorption temperature will generally be above about 50° C., more typically above about 70° C. and often above about 90° C. When recovering carboxylic acids such as citric or lactic acid, desorption temperatures above about 90° C. will be preferred.

Favored processes of the invention are conducted using a continuous contacting apparatus ("CCA"). For example, continuous contacting apparatuses which are useful in the invention include those such as the ISEP Continuous Contactor available from Advanced Separations Technology, Inc. (AST, Inc.), Lakeland, Fla., and are also generally described in U.S. Pat. No. 4,764,276 issued Aug. 16, 1988, U.S. Pat. No. 4,808,317 issued Feb. 28, 1989 and 4,522,726 issued Jun. 11, 1985. A brief description of such a CCA device as described in these patents is set forth below. For further details as to the design and operation of CCA's suitable for use in the invention, reference can be made to literature available from AST, Inc. including "The ISEP™ Principle Of Continuous Adsorption", and as well to the above-cited U.S. patents.

The preferred CCA for use in the present invention will be a liquid-solid contact apparatus including a plurality of chambers which are adapted to receive solid adsorbent material. The chambers have respective inlet and outlet ports, and are mounted for rotation about a central axis so as to advance the chambers past supply and discharge ports which cooperate with the inlet and outlet ports. In particular, liquid is supplied individually to inlet ports at the top of these chambers through conduits connected with a valve assembly above the chambers, which valve assembly provides a plurality of supply ports which cooperate with inlet ports of the chambers as they are advanced. Similarly, conduits connect the outlet port at the lower end of each chamber with a valve assembly below the chambers which provides discharge ports which cooperate with the outlet ports as the chambers are advanced. The valve assemblies include movable plates with slots that cover and uncover inlet ports as the plate rotates with the carousel. By varying the size of the slots in the plate and the location of the slots, the flow from the supply conduits into the chamber and flow from the chamber to the exhaust conduits can be controlled in a predetermined manner. The time during which liquid flows into and out of the chambers is a function of the speed of rotation of the chambers about the central axis.

More specifically, a preferred contacting device for use in the invention is shown generally in FIG. 1. The apparatus includes a rectangular frame 11 which supports a vertical drive shaft 12. A carousel 13 is mounted for rotation on the drive shaft. The carousel is fixed to the shaft and the shaft is driven by a motor 14 mounted on the frame 11. A plurality of cylindrical chambers 15 (e.g. 30 chambers) are mounted vertically on the carousel 13. The chambers are preferably arranged in staggered relation around the circumference of the carousel. Each of the chambers is filled with resin or other suitable solid adsorbent material according to the particular process being performed. As shown at the left side of FIG. 1 in cross-section, the solid adsorbent material 16 is preferably filled to about one-half the height of the chamber 15. An arrangement is provided on each chamber 15 for inserting and removing the solid material through the top of the container. Pipe fittings 17 and 18 are provided at inlet and outlet openings on the top and bottom, respectively, of each chamber 15. An upper valve body 19 and a lower valve body 20 are mounted over the drive shaft 12. The valve bodies 19 and 20 provide supply and discharge ports, respectively (e.g. 20 each). Individual conduits 21 and 22 connect the valve bodies 19 and 20 with the respective upper and lower pipe fittings 17 and 18, so as to allow cooperation of the supply and discharge ports of valve bodies 19 and 20 with the inlet and outlet ports of the chambers 15. Supply conduits 23 are mounted in the top of the frame 11 and extend upwardly from the valve body 19. Similarly, discharge conduits 24 extend downwardly from the lower valve body 19 to the frame 11. In this manner, as the carousel is rotated to advance the chambers 15, the inlet and outlet ports of the chambers 15 cooperate with the supply and discharge ports of the valve bodies 19 and 20 to provide advantageous means for circulating liquids through the chambers 15.

In accordance with one aspect of the invention, the apparatus of FIG. 1 will preferably be configured so as to include adsorption, rinse, and desorption zones, and optionally a regeneration zone. The adsorption zone can be conventionally operated so as to adsorb the material of interest, e.g. citric acid, onto an adsorptive resin contained within chambers 15 from a feed solution. Generally, a feed solution containing the citric acid will be passed countercurrent through the chambers 15 and over the resin so as to achieve substantial loading of the resin with citric acid as described previously A rinse zone can also be established and conventionally operated, in which water or another rinse material is passed countercurrent through the chambers and over the resin beds therein to remove salts or other undesired residues from the beds. It will be understood that the number of ports of the CCA dedicated to the adsorption and rinse zones may vary, and will be determined so as to maximize overall process economics. In addition, it will be understood that the advantageous use of product stream in the rinse zone as discussed above can be achieved by diverting a portion of the product from the desorption zone to the rinse zone. Specific illustrations of such configurations are discussed below in connection with the FIG. 3.

A feature of the present invention is the establishment of a desorption zone in which the resin beds within chambers 15 are heated and/or cooled by recirculation of liquid at appropriate temperatures and at appropriate times, so as to effectuate heat conservation and the recovery of highly concentrated desorbed product mediums.

Figure 2:
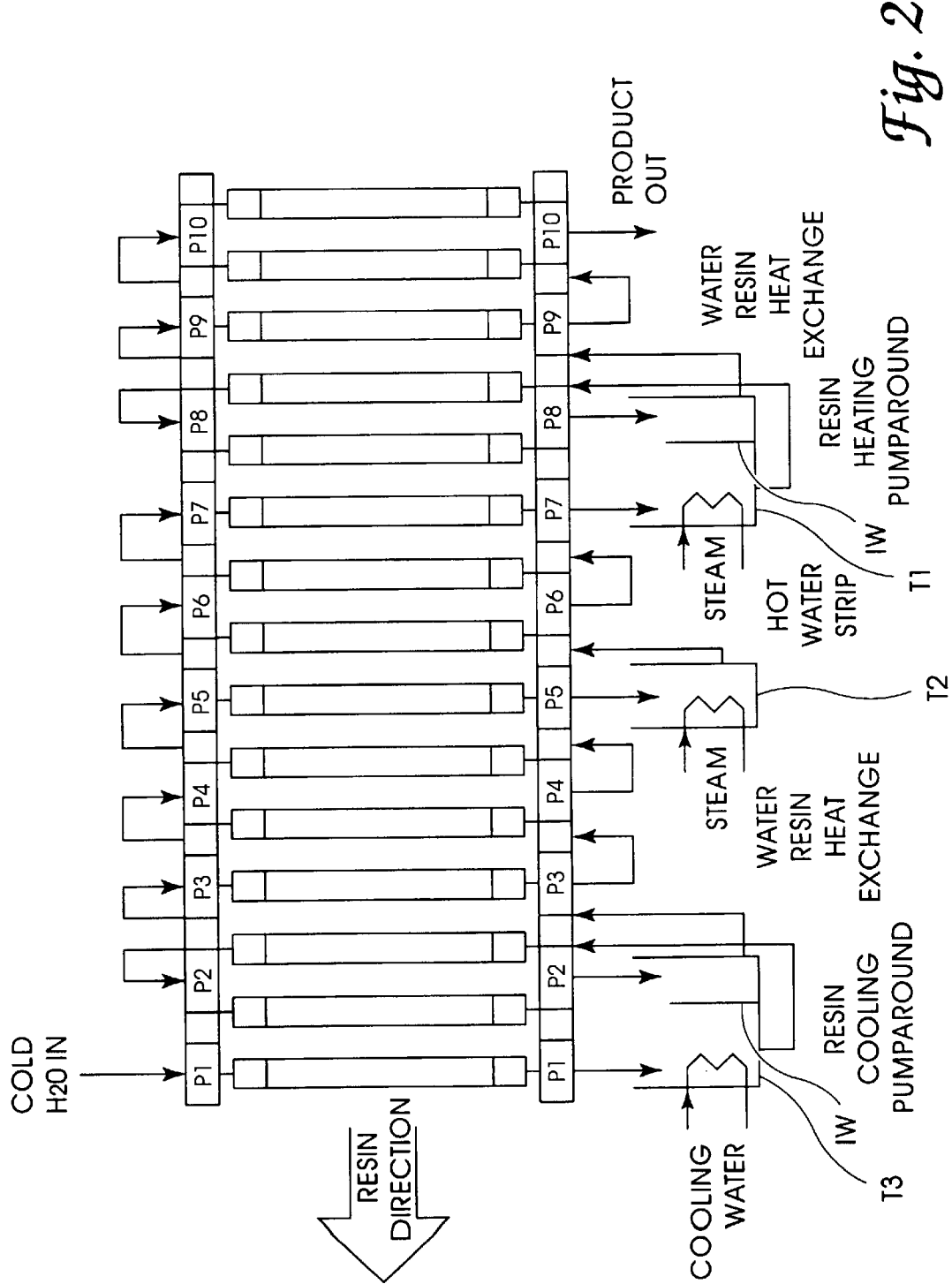
FIG. 2 is a schematic diagram of a desorption section of a continuous contacting apparatus which can be used in the present invention.

FIG. 2 is a schematic of one desorption zone configuration that demonstrates the aspects described above. This particular configuration can be used, for example, in the recovery of citric acid from a citric acid broth. After adsorption and optionally rinse steps, the chambers containing the resin beds would be entering the desorption zone at port P10. At this point, the resin beds are cold, e.g. exhibiting temperatures in the range of about 0° C. to about 30° C. The adsorbent resin will be loaded with citric acid, i.e. citric acid is adsorbed to the resin. The resin is then contacted in a countercurrent manner with hot citric acid solution leaving the system in ports P9 and P10 (this hot citric acid solution is produced as discussed below). The resin bed is heated as it moves through the P10 port and then through the P9 port, having a temperature of about 60° C. to about 90° C. when leaving the P9 port. The citric acid solution flows first through the P9 port exiting with a temperature of about 65° C. to about 95° C. and then through the P10 port exiting with a temperature of about 30° C. to about 70° C.

Upon entering port P8 from port P9, the resin is heated to some extent as discussed above, but has not yet reached the desired desorption temperature. In port P8, a hot citric acid solution at the desired temperature, typically about 70° C. to about 100° C., is recirculated to heat the bed to the temperature of the liquid. Preferably, at least two and one half bed volumes of heated citric acid solution are recirculated through the resin bed while at port P8 to accomplish this heating. The heated citric acid solution is obtained using a heat exchanger situated between ports P7 and P8 and effective to transfer heat into the solution. For example, in-line heat exchange can be accomplished by operably associating a heat exchanger with conduit running between ports P7 and P8. Preferably, however, the solution exiting port P7 is fed into a tank or other suitable reservoir "T1" equipped with a heat exchanger such as a steam-fed or electrically heated coil. The solution is collected and has a residence time in the tank sufficient to accomplish the desired heat transfer. The thus heated citric acid solution is then fed to port P8 to there heat the resin beds as discussed above. More specifically, as illustrated, upon exit from port P8, the citric acid solution enters a chamber in T1 separated by an internal wall "IW" from the heat exchange side of T1. The chambers are sized and the internal wall "IW" has a height such that a portion of the citric acid solution exiting port P8 spills back into the heat exchange side of T1 and a portion is fed on to port P9. Thus, at least a portion of the citric acid solution exiting port P8 is recirculated through the heat exchange zone in T1 and back into port P8 to further heat the resin bed therewith associated.

After the bed is heated in port P8, it proceeds through ports P7 and P6 where it is contacted with hot water at about the same temperature of the bed to extract or desorb the citric acid from the bed. As illustrated, a further heat exchanger is positioned to transfer heat to water immediately prior to its reaching port P6. Similar to the heat exchanger discussed above, this heat exchanger can be either an in-line exchanger or can be associated with a tank "T2" in which the exit feed from port P5 is collected.

As the bed continues through ports P5, P4, and P3, the bed is cooled by the countercurrent passing of water and the water is heated up. At this point, the temperature of the resin moving from port P3 will range from 5° C. to about 35° C. and the water exiting from port P5 will range from about 45° C. to about 80° C. Further washing of the resin is also accomplished by this water. When the bed reaches port P2, it is still not at the desired cold temperature and therefore a recirculation of a cold liquid (water in this case) is used to cool the bed to the desired temperature. Again, at least two and one half bed volumes of liquid are preferably recirculated to accomplish the cooling of the bed. As illustrated, a still further heat exchanger is positioned to remove heat from water prior to its reaching port P3. As with the heat exchangers discussed above, this heat exchanger can be either an in-line exchanger or can be associated with a tank "T3" having separate chambers into which the exit feeds from ports P1 and P2 are collected, respectfully. Similar to T1, T3 has a heat exchange chamber separated from another chamber by an internal wall "IW". The size of the chambers and the height of the internal wall are such that a portion of the solution exiting port P2 spills over into the heat exchange side of T3 wherein it is further cooled and recirculated back through port P2 to further cool the resin bed therewith associated. The remainder of the solution exiting port P2 is conducted on to port P3. In port P1, cold water is introduced for the final wash of the citric acid from the resin.

It will be understood that the number of ports allocated to each of the functions in the desorption zone can be varied depending upon flow rates required and relative heat capacities and heat transfer coefficients of the materials. For example, if the viscosity of any of the liquids is too high to permit recirculating the two and one half bed volumes in one port, it is possible to assign two ports to the recirculation. For example, in the case of recirculation heating it would be possible to use both ports P8 and P9 for this activity and leave only port P10 for heat transfer. Similarly, if ports P3, P4 and P5 are more than are needed for the heating of the liquid while simultaneously cooling the bed, these ports could be reduced to e.g. P4 and P5.

Of course, after exiting the desorption zone, the resin beds can optionally be subjected to a regeneration zone to prepare them for the next adsorption function. The regeneration zone can also be conventionally operated to remove residuals from the resin. For example, where a resin containing tertiary amine functions is employed, the resin may be treated with a basic material such as NaOH and subsequently rinsed with water.

It will be understood that it is not necessary to accomplish the recirculation cooling of the resin in the desorption or stripping section of the CCA. Rather, it is possible to obtain the required cooling of the resin by recirculating the liquid at the start of the adsorption section in a similar manner as the heating is accomplished near the start of the desorption section in port P8.

It will also be understood that the above-described heat and cooling concepts can be employed with stripping operations other than purely temperature adsorption/desorption processes. Ion exchange or solvent regeneration also can be combined with the temperature process. Thus, for example, after the temperature desorption as shown in FIG. 2, the resin beds could proceed from port P1 into a chemical stripping section (e.g. base, acid or solvent) to remove other adsorbed species before again entering the regeneration or adsorption section of the CCA.

Preferred processes of the invention conducted in the CCA will be carried out in a fashion which minimizes product loss and contaminants in the product, while maximizing the concentration of product in the product stream. In many ways these are competing interests, as in general terms many measures taken to increase the concentration of product in the product stream and decrease product contaminants will result in decreases in product recovery, and vice versa. For example, increasing the product concentration in the feed stream will generally lead to increased concentrations of product in the product stream; however, feed streams which are too rich in product will exceed the effective capacity of the resin and result in significant product loss. Similarly, decreasing the rate at which rinse streams are fed through the resin beds will provide product streams with higher product concentrations, but on the other hand can lead to increased contaminants in such product streams due to ineffective rinsing.

Desorption operations as discussed above can provide surprising and unexpectedly high levels of products such as citric acid in the recovered desorbed medium. For example, citric acid solutions exceeding about 12% by weight citric acid, and even up to about 14% or more citric acid, can be obtained using water as the desorbent, all while conserving and effectively utilizing heat energy applied to the desorption function. These highly enriched product streams can typically be obtained using concentrated feeds, for example about a 30% citric acid feed. However, fermentation broths often contain the product, for example citric or lactic acid, in a lower concentration, say, about 10% to about 15%. Thus, pre-concentration of this broth would be required to obtain a 30% product feed. Such pre-concentration measures are relatively costly, and are thus preferably avoided. In addition, as discussed above, highly pre-concentrated feeds can exceed the effective capacity of the resin and lead to product loss to waste.

Figure 3:
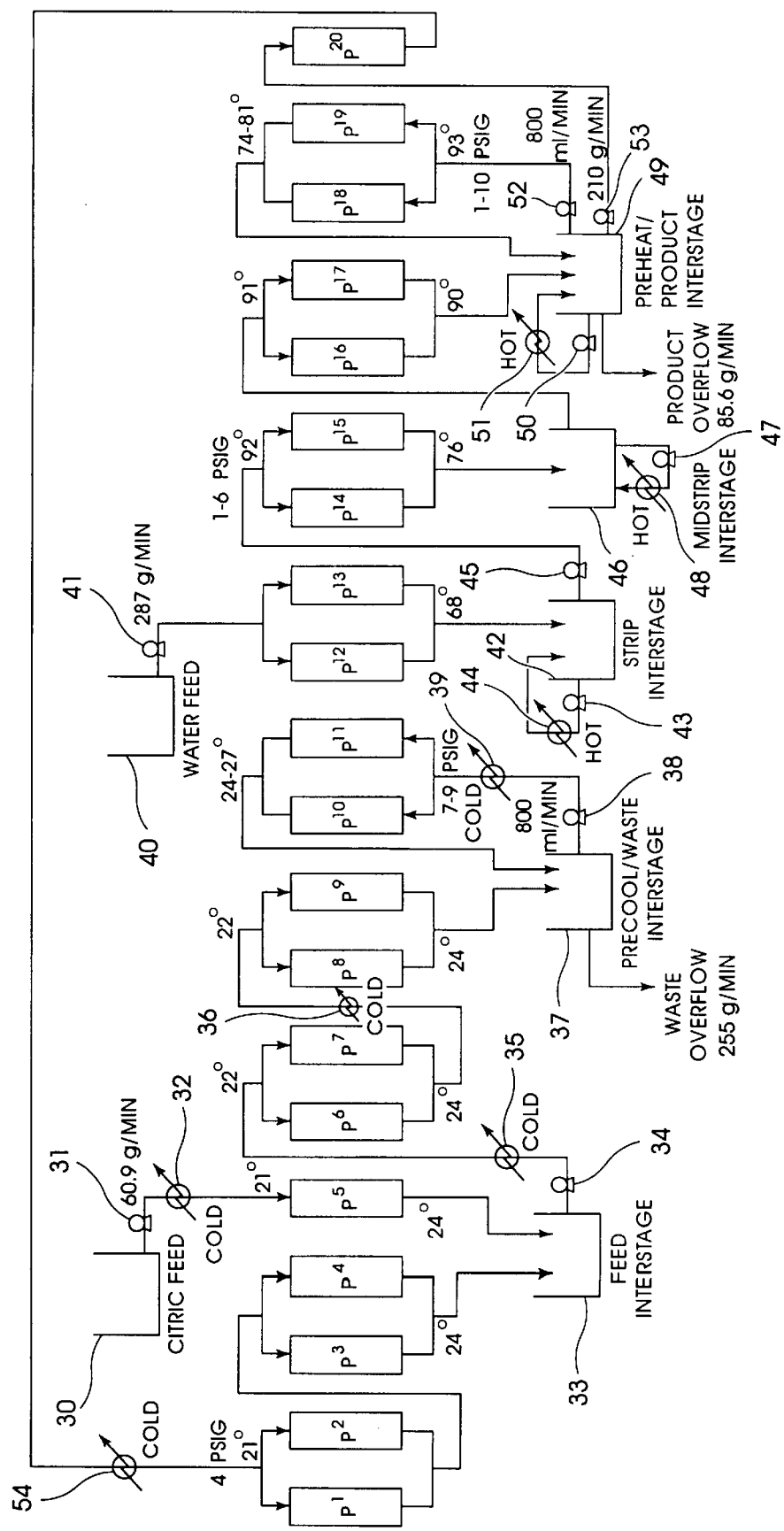
FIG. 3 is a schematic diagram illustrating a port configuration for a continuous contacting apparatus which can be used in the present invention.

As mentioned above, another feature of the invention relates to an adsorption-rinse-desorption process in which the product stream or at least a portion thereof is utilized in the rinse operation. These preferred processes provide an increase in the concentration of the product in the product stream, thus addressing the need for enriched product streams without the requirement of feed pre-concentration. FIG. 3 illustrates a configuration utilizing this aspect of the invention in a CCA such as that described above. In particular, runs utilizing the configuration of FIG. 3 were carried out in an ISEP L100 pilot-scale CCA available from AST, Inc. The operation of the device is essentially as described above for CCA'S, with the device having a stationary manifold with 20 ports and a carousel of 30 resin columns cooperating with the ports. The valving operation created isolates the columns from different fluid streams while maintaining continuous flow through the ports. The L100 pilot unit had glass columns (1 inch inner diameter, 350 ml volume), with polypropylene caps and 70 mesh screening to contain the resin. The upper and lower valve assemblies connected to the columns were constructed of polypropylene and 316 stainless steel. All connections throughout the apparatus were made with standard ¼ inch inner diameter polypropylene, polyethylene or Teflon tubing. The heat exchangers illustrated in FIG. 3 were either tube-and-shell or plate-and-frame heat exchangers. Low pressure steam was used for heating and chilled water (about 15° C.) or tap water (ambient temperature) was used for cooling. Peristaltic pumps with norprene tubing of various sizes (14–18) were used to transfer all solutions. The tubing was insulated in order to limit heat transfer with the surrounding environment.

Temperatures were measured in-line at the connection panel using ¼ inch stainless steel J-type thermocouples and recorded on a Yokogawa HR 1300 chart recorder. Pressures were measured in-line at the connection panel using stainless steel gauges. Flow rates were measured manually by weight over time (generally 30 minutes) at the various input or output ports.

Anhydrous USP/FCC grade citric acid, maltose monohydrate and anhydrous D-(+)-glucose, mixed anomers, and deionized water were used to make up the citric acid feed solutions. These solutions were prepared immediately prior to use to avoid potential bacterial growth.

REILLEX HP™ polymer was obtained from Reilly Industries, Inc. in water wet form. The resin was sieved to obtain beads in a size range of 30–60 mesh. The resin was then soaked in 15% citric acid solution overnight and transferred to the L100 glass columns. Each column was backwashed with several bed volumes of water to remove fines, then connected to the L100. A total of 10.5 L of citric acid swollen resin was charged to the 30 columns, which equated to about 7.55 L of water swollen resin or 2.10 kg dry resin.

FIG. 3 shows a schematic diagram of a preferred port configuration in the L100 which was used in the illustrative citric acid runs. The column rotation of the L100 was counter-current to solution flow, i.e. from right to left in FIG. 3. The measured temperatures, flow rates and insterstage tank positions are also shown in FIG. 3. Briefly describing the configuration, the flow pattern through the columns is generally downflow, with cold citric acid adsorption carried out in ports P5–P9, wash in ports P1–P4, and hot water desorption in ports P14–P17. Ports P10–P13 are used for cool-down of the resin after the desorption stage, while ports P18–P19 are used to preheat the loaded resins prior to the desorption stage. Port 20 is used to push remaining wash solution from the resin column.

More particularly, citric acid feed solution is fed from tank 30 using pump 31 through heat exchanger 32 (providing cooling) and into port P5. The stream exiting port P5 is fed to feed interstage tank 33. Solution from feed interstage tank 33 is fed using pump 34 through heat exchanger 35 (providing cooling) and into ports P6 and P7 in a parallel flow configuration. The streams exiting ports P6 and P7 is fed through heat exchanger 36 (providing cooling) and into ports P8 and P9 in parallel flow configuration. The streams exiting ports P8 and P9 are fed into precool/waste interstage tank 37. Solution from tank 37 is fed using pump 38 through heat exchanger 39 (providing cooling) and into ports P10 and P11, and the exit streams from ports P10 and P11 are directed back into tank 37. This "pump-around" provides precooling of the resin beds prior to their entry into the citric acid adsorption stage. Waste overflow also occurs at tank 37.

For the desorption stage, the desorption medium, e.g. water, is fed from feed tank 40 using pump 41 into ports P12 and P13 in parallel flow configuration. The exit streams from ports P12 and P13 flow into strip interstage tank 42. Pump 43 feeds solutions from tank 42 through heat exchanger 44 (providing heating) and back into tank 42. This pump-around through the heat exchanger heats the solutions in tank 42 for the desorption operations. It should be noted that strip interstage tank 42 and the other tanks employed in the configuration are preferably open to the atmosphere. This allows gasses evolved from the solutions, particularly when heated, to escape prior to entering the resin columns. This is advantageous for the reason that gasses flowing through the resin beds can cause channeling and interfere with the efficient operation of the device.

Heated solution from strip interstage tank 42 is fed using pump 45 into ports P14 and P15 in parallel flow. The exit streams from P14 and P15 are collected in midstrip interstage tank 46. Materials in tank 46 are also subjected to pump-around using pump 47 and heat exchanger 48 (providing heating). Materials from tank 46 are also fed to ports P16 and P17 in parallel flow configuration, and the corresponding exit streams are collected in preheat/product interstage tank 49. Materials in tank 49 are also subjected to pump-around using pump 50 and heat exchanger 51 (providing heating). A portion of the materials in tank 49 are recovered as product overflow. Another portion is fed using pump 52 into ports P18 and P19, and the corresponding exit streams are fed back into tank 49. The pump-around through P18 and P19 serves to preheat the resin beds prior to their entry into the desorption stages of the operation. Another portion of the materials in tank 49 is fed using pump 53 into port P20, which also preheats the resin beds at P20 to some extent.

In an important aspect of the present invention, the exit stream from port P20 is fed through heat exchanger 54 (providing cooling) and into the wash stage of the operation. Specifically, the port P20 exit stream is fed into ports P1 and P2 in parallel flow configuration. In the illustrated and preferred configuration, the product stream from port P20 serves exclusively as the wash agent in the wash operation. It will be understood, however, that this product stream could be used in conjunction with other wash agents fed to the wash stage, for example water. The collected exit streams from ports P1 and P2 are fed in parallel flow configuration into ports P3 and P4. Thus, in ports P1–P4, resin beds loaded with product, e.g. citric acid, are rinsed to remove non- or lesser-adsorbed materials such as sugars. The exit streams from ports P3 and P4 are collected in feed interstage tank 33, where they mix with the citric feed exiting port P5 and are processed along therewith as discussed beginning above.

In illustrative runs utilizing the configuration of FIG. 3, the L100 unit was run continuously for 3 hours before samples were collected, to facilitate the system reaching equilibrium or near equilibrium conditions prior to sampling. Output samples were collected over 30 minutes to ensure proper representation, and when more than one sample was taken, the time of collection was staggered with respect to the rotation rate so streams were not repeatedly coming from the same columns. In one such run, extending over 28 hours, a 14.7% citric acid feed containing 0.43% glucose and 2.03% maltose was fed to the system. The flow rates and temperatures of the flowing solutions at various key points in the system for this run are set out in FIG. 3. The product stream contained 9.73% citric acid on average (96% recovery) with 94% glucose and 97% maltose removal. In another similar run, except omitting the heat exchanger 32 and thus the cooling of the feed to column 5, the product stream contained 9.76% citric acid (98% recovery), and glucose and maltose removals were 96% and 98%, respectively. The processes thus provided highly enriched citric acid product mediums, with low sugar levels. These results compare very favorably to similar configurations of the L100 unit except using water in the rinse operation instead of product stream. In these water-wash runs, while the removal of sugars was effectively achieved, the product streams contained about 5.5% to 7% citric acid and the recovery of citric acid was generally below 90%.

While the invention has been illustrated and described in detail in the drawings and foregoing description, the same is to be considered as illustrative and not restrictive in character, it being understood that only the preferred embodiment has been shown and described and that all changes and modifications that come within the spirit of the invention are desired to be protected.

All publications cited herein are indicative of the level of skill in the art and are hereby incorporated by reference as if each had been individually incorporated by reference and fully set forth.

What is claimed is:

1. A thermal desorption process, comprising:

establishing a process wherein an amount of adsorbent is substantially loaded with an adsorbed product, the loaded adsorbent is rinsed with a rinse agent, and the loaded adsorbent is then treated with a heated desorbing agent to form a product-containing medium;

wherein the rinse agent contains an amount of the product to promote retention of the adsorbed product on the adsorbent; and wherein the product-containing medium is passed through a heated heat exchanger and through the same or another amount of product-loaded adsorbent, to enrich the product-containing medium in the product.

2. The process of claim 1 wherein the product is a carboxylic acid.

3. The process of claim 2 wherein the desorbing agent is an aqueous medium.

4. The process of claim 3 wherein the product is citric acid or lactic acid and the desorbing agent is water.

5. The process of claim 4 wherein the product is citric acid.

6. The process of claim 2 wherein the adsorbent is a cross-linked polymer resin containing tertiary amine groups.

7. The process of claim 4 wherein the adsorbent is a crosslinked polymer resin containing tertiary amine groups.

8. The process of claim 7 wherein the adsorbent is a pyridine-containing polymer resin.

9. The process of claim 7 wherein the polymer resin is crosslinked with divinylbenzene.

10. The process of claim 8 wherein the polymer resin is crosslinked with divinylbenzene.

11. The process of claim 10 wherein the polymer resin is a divinylbenzene crosslinked poly-2- or poly-4-vinylpyridine.

12. The process of claim 11 wherein the resin is in a macroreticular bead form.

13. The process of claim 12 wherein the resin is about 2% to 25% by weight crosslinked with divinylbenzene.

14. The process of claim 13 wherein the product is citric acid.

15. The process of claim 1, which comprises:

establishing a process wherein a plurality of contacting zones containing adsorbent are sequentially processed, the processing including substantially loading the adsorbent in the contacting zone with the adsorbed product, rinsing the adsorbent in the contacting zone with a rinse agent, and then treating the adsorbent in the contacting zone with a desorbing agent to form a product-containing medium;

wherein a portion of the product-containing medium from a prior-processed contacting zone is included in the rinse agent in the processing of a subsequent contacting zone, to decrease removal of the adsorbed product from the adsorbent during the rinsing step.

16. A thermal desorption process, comprising:

(a) desorbing a product from a solid adsorbent resin, said desorbing including:

(i) a first desorption step including passing a heated desorbent liquid through a first contacting zone containing a solid adsorbent resin having a product adsorbed thereto, so as to desorb adsorbed product from the resin and form a product-containing medium;

(ii) a heat exchange step after said first desorption step, including passing the product-containing medium through a heat exchange zone in which additional heat is transferred to the medium; and (iii) a second desorption step after said heat exchange step, including passing the product-containing medium through the same or another contacting zone containing solid adsorbent resin having an additional amount of the product adsorbed thereto, to desorb the product from the resin and enrich the product-containing medium in the product;

(b) including a portion of the product from step (a) in a liquid stream passed through a further contacting zone containing a solid adsorbent resin having an additional amount of the product adsorbed thereto.

17. The process of claim 16 wherein the product is a carboxylic acid and wherein in said second desorption step the product-containing medium is passed through another contacting zone.

18. The process of claim 17 wherein the desorbent liquid is an aqueous medium.

19. The process of claim 18 wherein the product is citric acid or lactic acid and the desorbent liquid is water.

20. The process of claim 19 wherein the product is citric acid.

21. The process of claim 16 wherein during said second desorption step, the heated desorbent liquid is passed through the same contacting zone as it was in said first desorption step, whereby heat transferred to the desorbent medium in said heat exchange step is transferred to the solid adsorbent during said second desorption step.

22. A thermal desorption process according to claim 16, comprising:

(a) providing a plurality of chambers having inlet ports and outlet ports and containing a solid adsorbent resin loaded with product;

(b) advancing the chambers sequentially past a plurality of supply ports to cooperate with the inlet ports and discharge ports to cooperate with the outlet ports;

(c) introducing a heated desorbent liquid into a first of the chambers through a first of the supply ports, the desorbent liquid passing over the adsorbent resin in the first chamber and exiting through a first of the discharge ports as a first product-containing medium;

(d) passing the first product-containing medium after step (c) through a heat exchange zone wherein it is heated;

(e) conducting the heated medium after step (d) through a second of the supply and into a second of the chambers, the product-containing medium passing over the loaded adsorbent resin in the second chamber and exiting through a second of the discharge ports as a second product-containing medium enriched in product as compared to the first product-containing medium.

23. The process of claim 22 wherein said product is a carboxylic acid.

24. The process of claim 23 wherein the product is citric acid.

25. The process of claim 22 wherein the desorbent liquid is an aqueous medium.

26. The process of claim 22 wherein said supply ports cooperate with said inlet ports and said discharge ports cooperate with said outlet ports so as to pass the desorbent liquid through said chambers in a countercurrent fashion.

27. The process of claim 22 wherein step (i) includes conducting the product-rich desorbent liquid after step (h) through a fourth and a fifth of said supply ports which precede said third supply port, and respectively into a fourth and fifth of said chambers, said desorbent liquid passing over and heating the adsorbent resin in said fourth and fifth chambers.

28. The process of claim 25 wherein said product is a carboxylic acid.

29. The process of claim 27 wherein the carboxylic acid is citric acid or lactic acid and the desorbent liquid is water.

30. The process of claim 23 wherein the desorbent liquid is an aqueous medium.

31. The process of claim 30 wherein said supply ports cooperate with said inlet ports and said discharge ports cooperate with said outlet ports so as to pass the desorbent liquid through said chambers in a countercurrent fashion.

32. The process of claim 31 wherein said product is a carboxylic acid.

33. The process of claim 32 wherein the carboxylic acid is citric acid or lactic acid and the desorbent liquid is water.

34. The process of claim 21, wherein at least a portion of the desorbent liquid after step (e) is passed again through the heat exchange zone of step (d) wherein it is cooled, and wherein the desorbent liquid is thereafter conducted again through said second chamber so as to cool the solid adsorbent resin therein.

35. A desorption process, comprising:

establishing a process wherein a plurality of contacting zones containing adsorbent are sequentially processed, the processing including substantially loading the adsorbent in the contacting zone with an adsorbed product, rinsing the adsorbent in the contacting zone with a rinse agent, and then treating the adsorbent in the contacting zone with a desorbing agent to form a product-containing medium;

wherein a portion of the product-containing medium from a prior-processed contacting zone is included in the rinse agent in the processing of a subsequent contacting zone to decrease removal of the adsorbed product from the adsorbent during the rinsing step.

36. The process of claim 35 wherein the product is a carboxylic acid.

37. The process of claim 36 wherein the desorbing agent is an aqueous medium.

38. The process of claim 37 wherein the product is citric acid or lactic acid and the desorbing agent is water.

39. The process of claim 38 wherein the product is citric acid.

40. The process of claim 36 wherein the adsorbent is a cross-linked polymer resin containing tertiary amine groups.

41. The process of claim 38 wherein the adsorbent is a crosslinked polymer resin containing tertiary amine groups.

42. The process of claim 41 wherein the adsorbent is a pyridine-containing polymer resin.

43. The process of claim 41 wherein the polymer resin is crosslinked with divinylbenzene.

44. The process of claim 42 wherein the polymer resin is crosslinked with divinylbenzene.

45. The process of claim 44 wherein the polymer resin is a divinylbenzene crosslinked poly-2- or poly-4-vinylpyridine.

46. The process of claim 45 wherein the resin is in a macroreticular bead form.

47. The process of claim 46 wherein the resin is about 2% to 25% by weight crosslinked with divinylbenzene.

48. The process of claim 47 wherein the product is citric acid.

49. The process of claim 35, comprising:

(a) providing a plurality of chambers having inlet ports and outlet ports and containing a solid adsorbent resin loaded with adsorbed product;

(b) advancing the chambers sequentially past a plurality of supply ports to cooperate with the inlet ports and discharge ports to cooperate with the outlet ports;

(c) introducing a desorbent liquid into a first of the chambers through a first of the supply ports, the desorbent liquid passing over the adsorbent resin in the first chamber and exiting through a first of the discharge ports as a product-containing medium;

(d) conducting the product-containing medium after step (c) through a second of the supply ports which precedes the first supply port, and into a second of the chambers, the desorbent liquid passing over and rinsing the adsorbent resin in the second chamber and exiting through a second of the discharge ports.

* * * * *